United States Patent [19]

Goel

[11] Patent Number: 4,657,939

[45] Date of Patent: Apr. 14, 1987

[54] TRIOLS FROM BICYCLIC AMIDE ACETALS AND CYANURIC ACID AND POLYURETHANES THEREFROM

[75] Inventor: Anil B. Goel, Worthington, Ohio

[73] Assignee: Ashland Oil, Inc., Ashland, Ky.

[21] Appl. No.: 874,192

[22] Filed: Jun. 13, 1986

Related U.S. Application Data

[63] Continuation of Ser. No. 722,822, Sep. 5, 1985, Pat. No. 4,617,391.

[51] Int. Cl.$^4$ .................. C08G 18/14; C08G 18/38; C08G 18/20
[52] U.S. Cl. .................. 521/163; 521/129; 528/52; 528/73; 528/75; 544/222
[58] Field of Search ............... 528/73, 52; 544/222; 521/163

[56] References Cited

U.S. PATENT DOCUMENTS

| | | | |
|---|---|---|---|
| 4,101,527 | 7/1978 | Cunningham et al. | 528/73 |
| 4,540,767 | 9/1985 | Goel et al. | 528/60 |
| 4,549,005 | 10/1985 | Goel | 528/53 |
| 4,558,113 | 12/1985 | Goel | 528/59 |
| 4,558,114 | 12/1985 | Goel | 528/73 |
| 4,562,240 | 12/1985 | Goel et al. | 528/73 |
| 4,569,959 | 2/1986 | Dunski et al. | 544/222 |
| 4,579,877 | 4/1986 | Goel et al. | 521/163 |
| 4,582,890 | 4/1986 | Tufts et al. | 528/60 |
| 4,584,363 | 4/1986 | Goel et al. | 528/73 |
| 4,594,397 | 6/1986 | Goel et al. | 525/528 |
| 4,601,995 | 7/1986 | Goel | 528/54 |
| 4,613,660 | 9/1986 | Goel et al. | 528/73 |

*Primary Examiner*—Herbert S. Cockeram
*Attorney, Agent, or Firm*—John F. Jones

[57] ABSTRACT

Novel triols which are useful for the formation of polyurethanes are produced by the reaction of a bicyclic amide acetal with cyanuric acid.

5 Claims, No Drawings

TRIOLS FROM BICYCLIC AMIDE ACETALS AND CYANURIC ACID AND POLYURETHANES THEREFROM

This is a continuation of U.S. Pat. Application Ser. No. 722,822 filed 9-5-85 now U.S. Pat. No. 4,617,391.

This invention relates to the process for production of novel triols by reaction of a bicyclic amide acetal with cyanuric acid and to the use of these triols in polyurethane formation.

There is no known prior art describing the reaction between bicyclic amide acetals and cyanuric acid to produce triols nor the use of these novel triols in the formation of polyurethanes by their reaction with polyisocyanates.

I have discovered a process for the production of novel triols containing cyanurate rings and amide groups by the reaction of bicyclic amide acetals with cyanuric acid. The reaction occurs rapidly and exothermically to produce the triols. The triols are useful, per se, or in combination with other polyols in the production of polyurethanes when reacted with polyisocyanates. The resulting polyurethanes are cross-linked by virtue of the triols and thus have higher temperature stability.

I have discovered that bicyclic amide acetals of Formula I

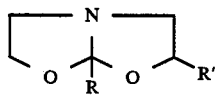

will react exothermically with cyanuric acid in molar ratio of about 3:1 of bicyclic amide acetal:cyanuric acid to give novel triols. In Formula I R represents hydrogen, an alkyl group having from 1 to 20 carbon atoms, an aryl group having from 6 to 12 carbon atoms or an alkaryl group having from 7 to 20 carbon atoms and R′ represents hydrogen, an alkyl group having from 1 to 15 carbon atoms, an aryl group having from 6 to 12 carbon atoms, an alkaryl group having from 7 to 15 carbon atoms, an alkyl ether group having from 1 to 20 carbon atoms or an aryl ether group having from 6 to 20 carbon atoms.

The process of this invention and the products produced thereby are illustrated in the following equation.

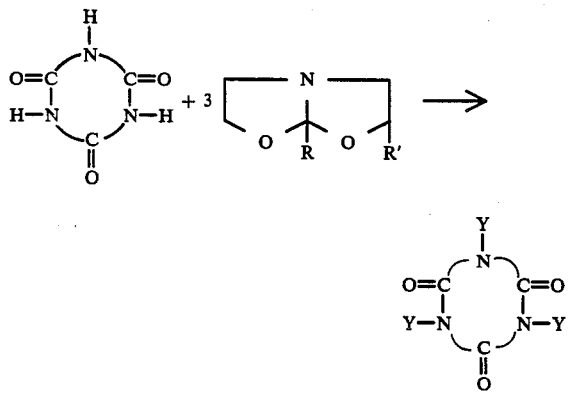

wherein Y represents $CH_2CH_2N(COR)CH_2CH(R')OH$.

The triols of this invention have been found to be miscible with other polyols such as propylene glycol, tripropylene glycol, and the like and can be used in polyurethane polymer synthesis by reaction with polyisocyanates. Thus, such polymers contain the triazine trione rings which are known to have improved properties such as thermal stability, rigidity, and the like. The triols of this invention can be used in polyurethane applications such as coatings, adhesives, foams, reaction injection molding (RIM) thermosets, composites, and the like.

Other polyols useful in this invention in addition to the novel triols of this invention in the production of polyurethanes include those having at least two hydroxyl groups per molecule and having equivalent weights falling in the range of from 20 to 5000. Specific polyols include butane diol, cyclohexane dimethanol, tripropylene glycol, amide diols, urethane diols, polyether polyols such as poly(tetremethylene ether) diols, poly(propylene ether) polyols, polyester polyols, and the like.

Polyhydroxy polyethers are suitable and preferably those having at least 2 hydroxyl groups per molecule. Polyhydroxy polyethers can be prepared by polymerization of epoxides such as ethylene oxide, propylene oxide, butylene oxide, tetrahydrofuran, styrene oxide, or epichlorohydrin either on their own or by chemical addition to other materials such as ethylene glycol, trimethylol propanes and 4,4′-dihydroxy diphenyl propane. Sucrose polyethers also may be used. Polybutadienes having hydroxyl groups as well as other known hydroxyl containing vinyl addition polymerized polymers can be used.

Hydroxyl containing polyesters, polythioethers, polyacetals, polycarbonates or polyesteramides of the types known for the formation of polyurethanes may also be used. Particularly useful other polyols for the present invention include the following representative aliphatic and aromatic polyhydric alcohols. Ethylene glycol, propylene glycol, trimethylene glycol, triethylene glycol, pentaethylene glycol, polyethylene glycol, 1,4-butanediol, diethylene glycol, dipropylene glycol, 2,2-dimethyl-1,3-propanediol, hexamethylene glycol, 1,4-cyclohexane dimethanol, xylene alcohols, ethyl resorcinol, propyl resorcinol, 2,4-dimethyl resorcinol, 3,6-dimethyl-1,2,4-benzene triol, ethyl pyrogallol, 2,4-dimethyl-1,4-dihydroxy naphthalene, 3-methyl-1,4,5-naphthalene triol, dimethylol toluene, dimethylol xylene, bis-hydroxy ethyl or bis-hydroxy propyl ethers of resorcinol, catechol, or hydroquinones, 1,5-dihydroxy naphthalene, 4,4′-isopropylidene-bis-phenol, and the like.

The polyisocyanates useful in the preparation of polyurethanes from the triols of this invention and mixtures of the triols and other polyols include organic isocyanates having at least two isocyanate groups per molecule. The polyisocyanates can be of low, high or intermediate molecular weight and can be any of a wide variety of organic polyisocyanates including ethylene diisocyanate trimethylene diisocyanate, dodecamethylene diisocyanate hexamethylene diisocyanate, hexamethylene diisocyanate trimer, tetraethylene diisocyanate, pentamethylene diisocyanate, propylene-1,2-diisocyanate, 2,3-dimethyl tetramethylene diisocyanate, butylene-1,2-diisocyanate, butylene-1,3-diisocyanate, 1,4-diisocyanato cyclohexane, cyclopentene-1,3- diisocyanate, p-phenylene diisocyanate, 1-methyl phenylene-2,4-diisocyanate, naphthalene-1,4-diisocyanate, toluene diisocyanate, diphenyl-4,4'-diisocyanate, toluene diisocyanate, benzene-1,2,4-triisocyanate, xylene-1,4-diisocyanate, xylylene-1,3-diisocyanate, 4,4'-diphenylene methane diisocyanate, 4,4'-diphenylene propane diisocyanate, 1,2,3,4-tetraisocyanato butane, butane-1,2,3-triisocyanate, polymethylene polyphenyl isocyanate, and other polyisocyanates having an isocyanate functionality of at least two which are more fully disclosed in U.S. Pat. Nos. 3,350,362 and 3,382,215. Polyisocyanates which are polymeric in nature including isocyanate prepolymers of all types are included in this invention.

The process of this invention is conveniently carried out at a temperature in the range of from about 20 degrees C. to about 200 degrees C. and at a pressure in the range of from about 1 atmosphere to about 50 atmospheres.

My invention is further illustrated in the following representative examples.

EXAMPLE 1

To 87.6g of cyanuric acid kept in a three-neck flask equipped with a mechanical stirrer, a thermometer with a temperature controller, a condenser and nitrogen inlet was added 267 g of a bicyclic amide acetal of Formula I in which R is methyl and 40 is hydrogen and the mixture was stirred under a nitrogen atmosphere. An exothermic reaction occurred within 15 minutes of commencement of the stirring and the reaction temperature rose to about 165 degrees C. The reaction mixture was then stirred for about three hours at 110–130 degrees C. The resulting highly viscous paste (glass) trial was found to have infrared bands at 3350–3400 cm−1 (OH groups) and 1600–1700 cm−1 (amide and cyanurate groups). The hydroxyl number for the product was determined to be 312. The product was found to be miscible with polyols such as propylene glycol and tripropylene glycol.

EXAMPLE 2

A solution of 32.2 g of tripropylene glycol, 10.0 g of the triol of Example 1 and 0.2 g of N,N',N"-tris(dimethylaminopropyl) hexahydrotriazine (catalyst) was degassed on a rotary evaporator and mixed with 65.1 g of liquid methylene bis(phenyl isocyanate) (NCO equivalent weight of about 144) This mixture was poured into a mold prepared from two silicone mold release coated glass plates held apart by ⅛inch thick spacers. The mold was placed in an oven at 100 degrees C. for one hour to give a solid polymer sheet. The sheet was found to have a notched izod impact strength (ASTM D-256) of 0.8 foot pounds/inch of notch, a flexural strength (ASTM D-790) of 16,559 psi and a flexural modulus of 352,907 psi.

EXAMPLE 3

The procedure of Example 2 was followed using 23 g of dipropylene glycol, 10 g of the triol of Example 1, 10 g of liquid diglycidyl ether of Bisphenol-A (epoxy equivalent weight of 185), 0.8g of tetraalkylammonium chloride and mixed with 90 g of isocyanate prepolymer obtained by reacting 90% liquid methylene bis(phenyl isocyanate) with 10% of carboxylic acid terminated polyacrylonitrile-butadiene rubber (18% acrylonitrile) at 100 degrees C. for one hour. The polymer obtained after one hour at 100 degrees C. followed by one hour at 130 degrees C. postcuring was found to have a notched izod impact strength of 1.1 foot pounds/inch of notch, an unnotched izod impact strength of greater than 14 foot pounds/inch, a heat distortion temperature (ASTM D-648) of 118 degrees C., a flexural strength of 19,125 psi and a flexural modulus of 398,750 psi.

EXAMPLE 4

The procedure of Example 2 was followed using the solution of 15 g of the triol of Example 1 and 85 g of poly(terephthalic ester) polyol (Chardol 570 from Chardnol Corporation, hydroxy number 350) prepared at 60 degrees C. and mixing with 0.4 g of the tertiary amine catalyst of Example 2 and 90 g of liquid methylene bis(phenyl isocyanate). The polymer sheet obtained after the curing at 110 degrees C. for one hour was found to have an izod impact strength of 0.9 foot pounds/inch of notch, a heat distortion temperature of 87 degrees C., a flexural strength of 18,035 psi and a flexural modulus of 417,232 psi.

EXAMPLE 5

The procedure of Example 2 was followed using 14 g of propylene glycol, 6 g of dipropylene glycol, 10 g of the triol of Example 1, 14 g of grafted poly(styrene-propylene oxide) triol (5000 molecular weight), 0.5 g of the tertiary amine catalyst of Example 2 and 95 g of the diisocyanate. The resulting polymer sheet was found to have a notched izod impact strength of 1 4 foot pounds/inch of notch, an unnotched izod impact strength of greater than 17 foot pounds/inch, a heat distortion temperature of 114 degrees C., a flexural strength of 17,155 psi and a flexural modulus of 372,449 psi.

EXAMPLE 6

This experiment demonstrates the use of the triol of Example 1 in the synthesis of a polyurethane structural foam. A solution of 25 g of the triol of Example 1 and 100 g of poly(terephthalic ester) polyol (Chardol 560 from Chardnol Corporation, hydroxy number 447) was prepared. A 15 g portion of this was mixed with 0.3 g of the tertiary amine catalyst of Example 2, 0.4 g of silicone surfactant (Dow Corning DC 193), 5.4 g of trichlorofluoromethane (Freon 11 B from DuPont) and the mixture was stirred rapidly with 21 g of liquid polymeric methylene bis(phenyl isocyanate) (NCO equivalent weight of 144). Foaming of the mixture occurred with the following characteristics: cream time of 20 seconds, rise time of 40 seconds, and tack free time of 48 seconds. The foam was postcured at 120 degrees C. for five minutes. The final foam was found to have a density of 1.8 pounds per cubic foot, a compressive strength (rise direction) of 16.8 psi and compressive strength (width direction) of 14 psi.

EXAMPLE 7

The procedure of Example 6 was followed using 15 g of the polyol mixture of Example 6, 0.3 g of the tertiary amine catalyst, 0.4 g of silicone surfactant DC 193, 7.2 g of talc filler, 5.5 g of Freon 11 B and 20 g of polymeric methylene bis(phenyl isocyanate). The mixture was stirred for five seconds and the foaming characteristics were: cream time 18 seconds, rise time 40 seconds and tack free time 46 seconds. The density of the foam was found to be 2.0 pounds per cubic foot with an average compressive strength of 17 pounds per cubic foot.

I claim:

1. The polyurethane produced by the reaction of a polyisocyanate with a triol resulting from the reaction of a bicyclic amide acetal with cyanuric acid at a temperature of from about 20° C. to about 200° C. and at a pressure in the range of from about 1 atmosphere to about 50 atmospheres.

2. The polyurethane of claim 1 wherein the molar ratio of bicyclic amide acetal to cyanuric acid used in the preparation of the triol is about 1:3.

3. The polyurethane of claim 2 wherein the bicyclic amide acetal is one having the formula

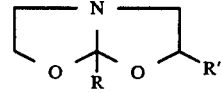

wherein R represents hydrogen, an alkly group having from 1 to 20 carbon atoms, an aryl group having from 6 to 12 carbon atoms or an alkaryl group having from 7 to 20 carbon atoms and R' represents hydrogen, an alkyl group having from 1 to 15 carbon atoms, an aryl group having from 6 to 12 carbon atoms, an alkaryl group having from 7 to 15 carbon atoms, an alkyl ether group having from 1 to 20 carbon atoms or an aryl ether group having from 6 to 20 carbon atoms.

4. The polyurethane of claim 3 wherein the bicyclic amide acetal is one in which R is methyl and R' is hydrogen.

5. The polyurethane of claim 4 wherein the polyisocyanate is methylend bis (phenyl isocyanate).

* * * * *